(12) United States Patent
Osawa (10) Patent No.: US 12,310,791 B2
(45) Date of Patent: May 27, 2025

(54) ULTRASOUND PROBE AND ULTRASOUND DIAGNOSTIC APPARATUS

(71) Applicant: FUJIFILM Corporation, Tokyo (JP)

(72) Inventor: Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 13 days.

(21) Appl. No.: 18/471,637

(22) Filed: Sep. 21, 2023

(65) Prior Publication Data
US 2024/0099693 A1 Mar. 28, 2024

(30) Foreign Application Priority Data
Sep. 22, 2022 (JP) .................. 2022-151549

(51) Int. Cl.
*A61B 8/00* (2006.01)
*B06B 1/06* (2006.01)

(52) U.S. Cl.
CPC ............ *A61B 8/4444* (2013.01); *A61B 8/546* (2013.01); *B06B 1/067* (2013.01); *B06B 1/0681* (2013.01); *B06B 1/0685* (2013.01)

(58) Field of Classification Search
CPC ...... B06B 1/067; B06B 1/0681; B06B 1/0685
See application file for complete search history.

(56) References Cited

U.S. PATENT DOCUMENTS

| | | | |
|---|---|---|---|
| 5,410,208 A * | 4/1995 | Walters | B06B 1/0622 310/369 |
| 6,107,722 A * | 8/2000 | Thurn | B06B 1/067 310/326 |
| 2008/0224567 A1 | 9/2008 | Sugiura et al. | |

(Continued)

FOREIGN PATENT DOCUMENTS

| | | |
|---|---|---|
| JP | 2000-184497 A | 6/2000 |
| JP | 2004-184423 A | 7/2004 |

(Continued)

OTHER PUBLICATIONS

The extended European search report issued by the European Patent Office on Feb. 19, 2024, which corresponds to European Patent Application No. 23198841.4-1001 and is related to U.S. Appl. No. 18/471,637.

*Primary Examiner* — Colin T. Sakamoto
(74) *Attorney, Agent, or Firm* — Studebaker Brackett PLLC (57) ABSTRACT

An ultrasound probe includes: vibrators arranged in a left-right direction; a support portion that supports a second surface opposite to a first surface located on a side on which the vibrator transmits and receives an ultrasound wave; an acoustic lens disposed on a side opposite to a support portion side with respect to the vibrator; an acoustic matching portion disposed between the vibrator and the acoustic lens; and a connection portion that connects the support portion and at least a partial region of one or both of a first end surface and a second end surface to each other, the first end surface and the second end surface being defined by both end surfaces of the acoustic matching portion in a front-rear direction intersecting the left-right direction and an up-down direction. The support portion and the connection portion each have a thermal conductivity higher than that of the acoustic lens.

16 Claims, 6 Drawing Sheets (56) References Cited

U.S. PATENT DOCUMENTS

| | | | |
|---|---|---|---|
| 2008/0312537 A1* | 12/2008 | Hyuga | ............... B06B 1/0622 |
| | | | 600/459 |
| 2012/0038248 A1 | 2/2012 | Mueller et al. | |
| 2015/0128723 A1 | 5/2015 | Satou et al. | |
| 2020/0376520 A1 | 12/2020 | Chen et al. | |

FOREIGN PATENT DOCUMENTS

| | | |
|---|---|---|
| JP | 2008-187355 A | 8/2008 |
| JP | 2012-513714 A | 6/2012 |
| JP | 3224928 U | 1/2020 |
| WO | 2013/183292 A1 | 12/2013 |

* cited by examiner

ULTRASOUND PROBE AND ULTRASOUND DIAGNOSTIC APPARATUS

CROSS-REFERENCE TO RELATED APPLICATIONS

This application is based upon and claims the benefit of priority from prior Japanese patent application No. 2022-151549, filed on Sep. 22, 2022, the entire contents of which are incorporated herein by reference.

BACKGROUND OF THE INVENTION

1. Field of the Invention

The present invention relates to an ultrasound probe and an ultrasound diagnostic apparatus.

2. Description of the Related Art

JP2004-184423A describes an ultrasound transmitter and receiver comprising a piezoelectric body, an acoustic matching layer provided on the piezoelectric body, a protective portion that is in contact with at least a part of a side surface of the acoustic matching layer and that is provided at a fixed position with respect to the piezoelectric body, a back surface load material that is disposed on a back surface of the piezoelectric body and that attenuates an ultrasound wave radiated from the piezoelectric body in a back surface direction, in which the protective portion is composed of a part of the back surface load material and is integrated with the back surface load material.

JP03224928Y describes an ultrasound transducer in which an entire combined structure of a piezoelectric body and of an acoustic impedance matching layer is fixed to an outer shell by a vibration damping body, and the piezoelectric body and the acoustic impedance matching layer are surrounded by the vibration damping body.

JP2012-513714A describes an ultrasound converter comprising a matching body, a compensating body inserted between the matching body and a piezoelectric converter element, and an attenuation element, in which the attenuation element is configured to surround the matching body on a radiation side facing a fluid medium and to surround the matching body and the compensating body in a radial direction.

WO2013/183292A describes an ultrasound wave transmitter and receiver comprising a piezoelectric body, an acoustic matching body, and an insulating vibration damping member, in which the insulating vibration damping member covers an outer surface of the piezoelectric body.

JP2008-187355A describes an ultrasound sensor comprising an acoustic matching member that receives an ultrasound wave transmitted from an ultrasound generating element and directed ahead of a vehicle and reflected in a detected object existing in front of the vehicle and that transfers a vibration to a piezoelectric element, the piezoelectric element that detects the vibration transferred from the acoustic matching member, and a vibration attenuation member provided between a side surface of the acoustic matching member and a housing.

SUMMARY OF THE INVENTION

In an ultrasound diagnostic apparatus for a medical use, an ultrasound image is generated by transmitting an ultrasound beam from an ultrasound probe toward a subject under examination, receiving an ultrasound echo from the subject under examination through the ultrasound probe, and electrically processing a reception signal thereof. In recent years, with the advancement in performance of the ultrasound probe and the ultrasound diagnostic apparatus, various types of driving have been applied to a vibrator inside the ultrasound probe. As a result, there is a tendency for an increased amount of heat generation near a contact surface of the ultrasound probe with the subject under examination. Therefore, it is required to prevent the heat generated in the ultrasound probe from being transferred to the subject under examination. JP2004-184423A, JP03224928Y, JP2012-513714A, WO2013/183292A, and JP2008-187355A do not pertain to technologies that assume an ultrasound diagnostic apparatus for a medical use.

An object of the present disclosure is to provide an ultrasound probe capable of restraining heat generated near a contact surface with a subject under examination from being transferred to the subject under examination, and an ultrasound diagnostic apparatus comprising the same.

According to one aspect of the present invention, there is provided an ultrasound probe comprising: a plurality of vibrators that are arranged in a first direction, each vibrator having a first surface which is located on a side on which the vibrator transmits and receives an ultrasound wave and a second surface opposite to the first surface; a support portion that supports the second surface of the vibrator; an acoustic lens that is disposed on a side opposite to a support portion side with respect to the vibrator; an acoustic matching portion that is disposed between the vibrator and the acoustic lens; and a connection portion that connects the support portion and at least a partial region of one or both of a first end surface and a second end surface to each other, the first end surface and the second end surface being defined respectively by both end surfaces of the acoustic matching portion in a second direction intersecting the first direction and a direction from the acoustic lens toward the vibrator, in which the support portion and the connection portion each have a thermal conductivity higher than a thermal conductivity of the acoustic lens.

According to one aspect of the present invention, there is provided an ultrasound diagnostic apparatus comprising: the ultrasound probe described above.

According to the present disclosure, it is possible to provide an ultrasound probe capable of restraining heat generated near a contact surface with a subject under examination from being transferred to the subject under examination, and an ultrasound diagnostic apparatus comprising the same.

DESCRIPTION OF THE PREFERRED EMBODIMENTS

Figure 1:
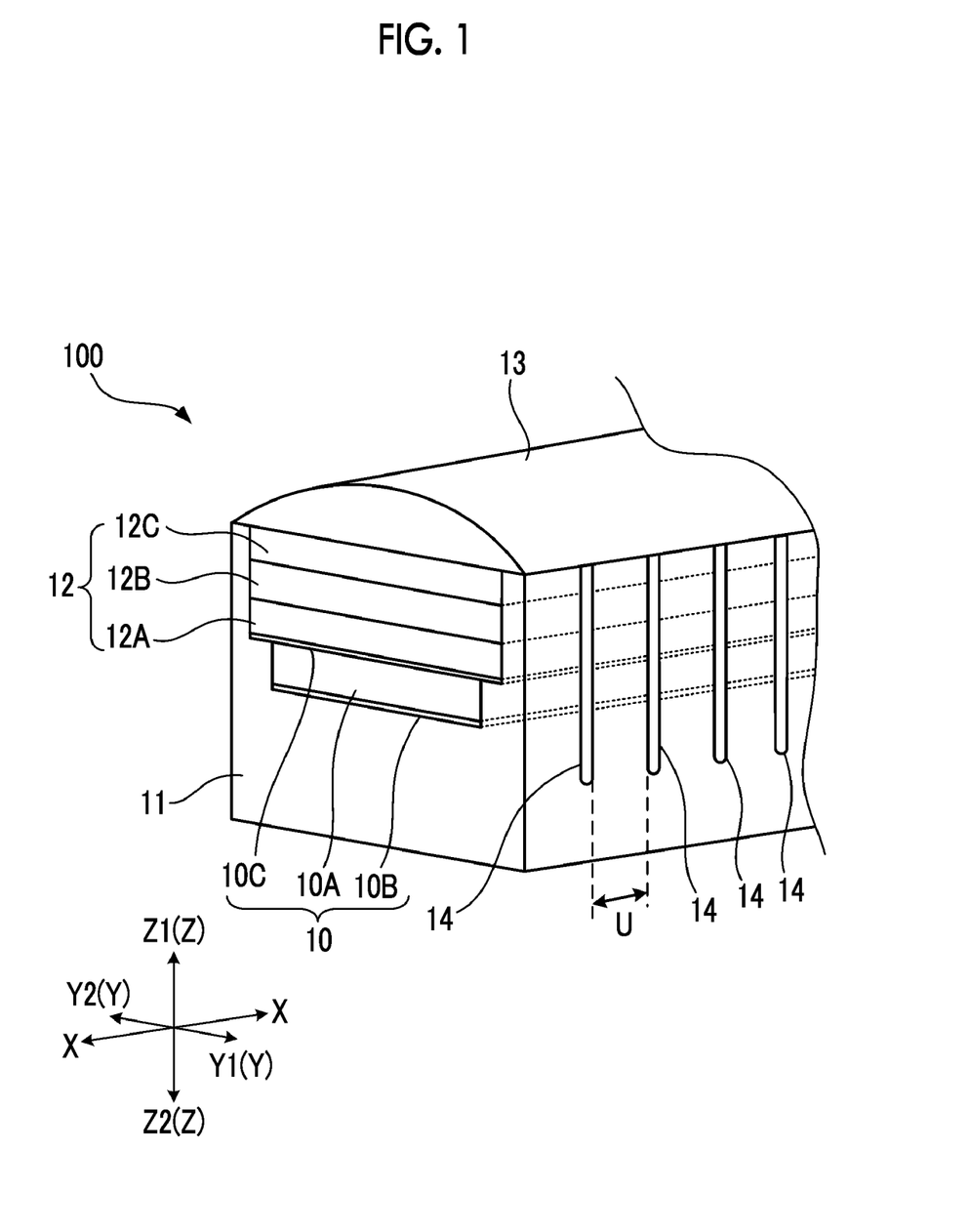
FIG. 1 is a perspective view partially showing a distal end part of an ultrasound probe 100 of one aspect according to the present disclosure.

FIG. 1 is a perspective view partially showing a distal end part of an ultrasound probe 100 of one aspect according to the present disclosure. FIG. 1 shows three directions (a left-right direction X, a front-rear direction Y, and an up-down direction Z) that are orthogonal to each other as directions of the ultrasound probe 100. One of the up-down direction Z is referred to as an upward direction Z1, and a direction opposite to the upward direction Z1 is referred to as a downward direction Z2. One of the front-rear direction Y is referred to as a rearward direction Y1, and a direction opposite to the rearward direction Y1 is referred to as a forward direction Y2. The ultrasound probe 100 is used by bringing an upper-side end surface thereof into contact with a subject under examination. The left-right direction X and the front-rear direction Y are each a direction along a plane (one of the planes intersecting the up-down direction Z) perpendicular to the up-down direction Z. In the present specification, the left-right direction X constitutes a first direction, the front-rear direction Y constitutes a second direction, and the up-down direction Z constitutes a direction from an acoustic lens 13 toward a vibrator 10, which will be described below. The front-rear direction Y is a direction intersecting the left-right direction X and the up-down direction Z.

The ultrasound probe 100 is an image generation device provided in the ultrasound diagnostic apparatus. The ultrasound diagnostic apparatus includes a device that generates and records an ultrasound image while bringing the ultrasound probe 100 into proximity with an outer surface of the subject under examination, a device that generates and records an ultrasound image while bringing the ultrasound probe 100 incorporated into an insertion part distal end of an endoscope into proximity with an organ of the subject under examination, or the like.

As shown in FIG. 1, the ultrasound probe 100 comprises a plurality of units U arranged in the left-right direction X, and an acoustic lens 13 provided on an upper side with respect to the plurality of units U and common to the plurality of units U. Adjacent units U are separated by a separation layer 14. The separation layer 14 is formed of an insulating resin material or the like. In the unit U, a width in the front-rear direction Y is greater than the width in the left-right direction X.

The unit U comprises the vibrator 10, an acoustic matching portion 12 disposed on the upper side with respect to the vibrator 10, and a functional part 11 provided around the vibrator 10 and the acoustic matching portion 12. Although not shown in FIG. 1, the acoustic lens 13, the plurality of units U, and the separation layer 14 are supported by a case 15 (see FIG. 2).

The vibrator 10 comprises a piezoelectric body 10A, a signal electrode 10B stuck to a lower-side surface of the piezoelectric body 10A, and a ground electrode 10C stuck to an upper-side surface of the piezoelectric body 10A. The piezoelectric body 10A generates an ultrasound wave in response to a voltage application and generates a reception voltage in a case where a reflected wave of the ultrasound wave is received. The piezoelectric body 10A is made of a piezoelectric ceramics, such as lead zirconate titanate (PZT), or a piezoelectric material, such as a polymer material, like polyvinylidene fluoride (PVDF) or the like. The piezoelectric body 10A may be composed of capacitive micro ultrasound transducers (CMUT), which are based on a semiconductor material, or the like.

The acoustic matching portion 12 is provided in order to efficiently transmit and receive ultrasound waves by matching acoustic impedances of the piezoelectric body 10A and the subject under examination. The acoustic matching portion 12 is preferably formed of a material having an acoustic impedance that is a value lower than the acoustic impedance of the piezoelectric body 10A and higher than the acoustic impedance of the subject under examination.

In the present embodiment, the acoustic matching portion 12 is formed by laminating a plurality of layers formed of such a material in the up-down direction Z. Specifically, the acoustic matching portion 12 comprises a first acoustic matching layer 12A stuck to an upper-side surface of the vibrator 10, a second acoustic matching layer 12B stuck to an upper-side surface of the first acoustic matching layer 12A, and a third acoustic matching layer 12C stuck to an upper-side surface of the second acoustic matching layer 12B. It is preferable that the acoustic matching portion 12 has a layered structure in which the acoustic impedance decreases in a stepwise manner from the vibrator 10 toward the subject under examination.

The acoustic lens 13 is provided in order to improve a resolving power by using refraction to focus the ultrasound beam. The acoustic lens 13 is generally composed of a convex type. The acoustic lens 13 is made of, for example, a silicone resin or plastic. The acoustic lens 13 is stuck to upper surfaces of the acoustic matching portions 12 in all the units U and an upper surface of the separation layer 14 between the units U with an adhesive or the like.

In the ultrasound probe 100, by applying a pulsed or continuous wave-like voltage between the ground electrodes 10C and the signal electrodes 10B of a plurality of the vibrators 10, each of the piezoelectric bodies 10A expands and contracts to generate a pulsed or continuous wave-like ultrasound wave. In a case where these ultrasound waves are incident on the subject under examination via the acoustic matching portion 12 and the acoustic lens 13, the ultrasound waves are combined with each other to form an ultrasound beam and propagate through the subject under examination. In a case where an ultrasound echo propagating through and reflected in the subject under examination is incident on each of the piezoelectric bodies 10A via the acoustic lens 13 and the acoustic matching portion 12, each of the piezoelectric bodies 10A is deformed, and in response to this deformation, a signal voltage is generated between the ground electrode 10C and the signal electrode 10B. The signal voltage generated in the plurality of vibrators 10 is extracted from between the ground electrode 10C and the signal electrode 10B of each of the vibrators 10 and received as a reception signal, and an ultrasound image is generated based on the reception signal.

Figure 2:
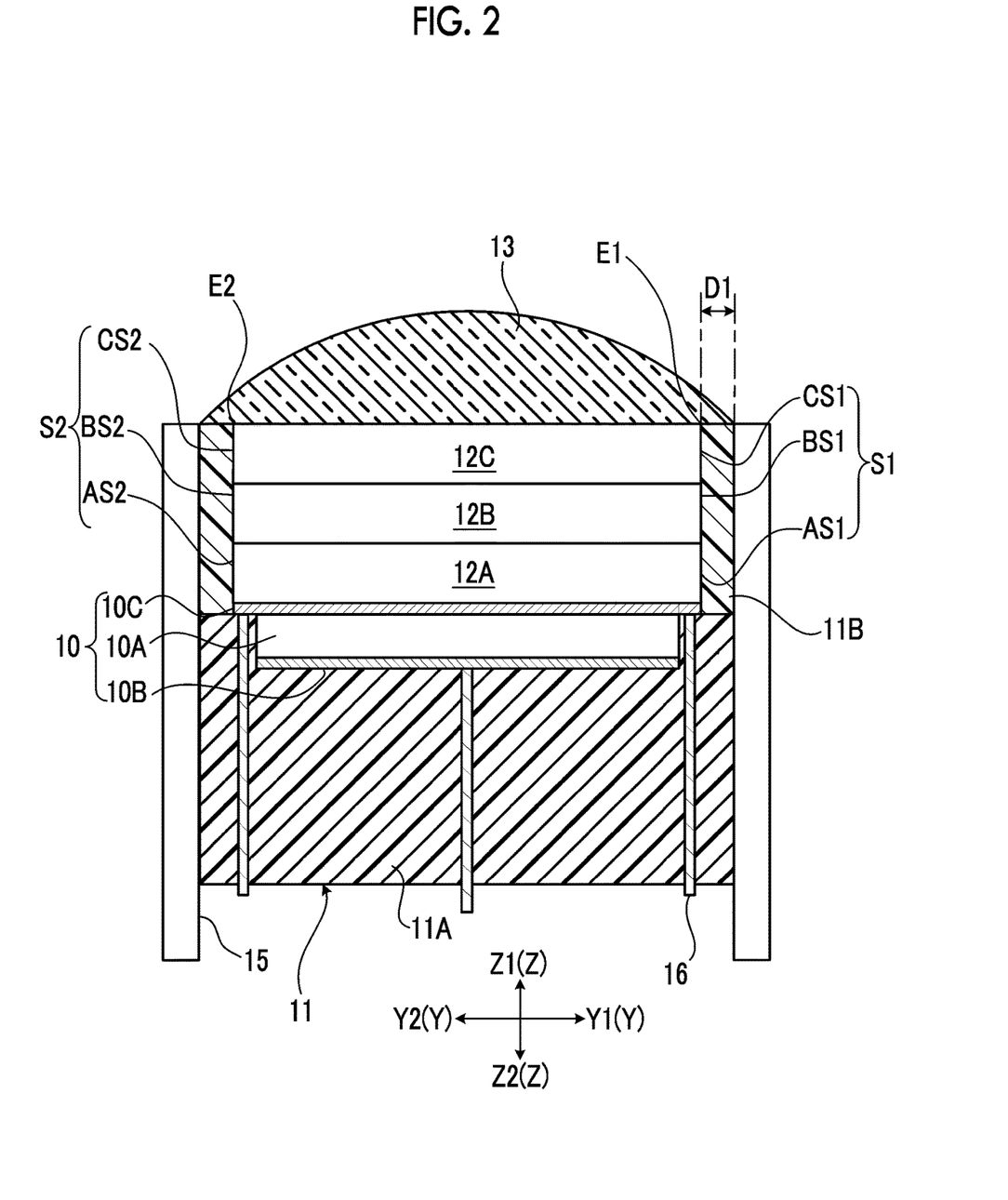
FIG. 2 is a schematic view showing a cross-section of a unit U perpendicular to a left-right direction X.

FIG. 2 is a schematic view showing a cross-section of the unit U perpendicular to the left-right direction X. As shown in FIG. 2, the functional part 11 comprises a support portion 11A that supports a second surface (lower-side surface) opposite to a first surface (upper-side surface) which is located on a side on which the vibrator 10 transmits and receives ultrasound waves, and a connection portion 11B that connects the support portion 11A and at least a part of the acoustic matching portion 12 to each other. The support portion 11A supports a lower surface of the vibrator 10 by being in contact with a lower surface of the signal electrode 10B, front and rear end surfaces of the piezoelectric body 10A, and lower surfaces of both front and rear end parts of the ground electrode 10C.

FIG. 2 shows, as both end surfaces of the acoustic matching portion 12 in the front-rear direction Y, a first end surface S1 consisting of a rear end surface AS1 of the first acoustic matching layer 12A, a rear end surface BS1 of the second acoustic matching layer 12B, and a rear end surface CS1 of the third acoustic matching layer 12C, and a second end surface S2 consisting of a front end surface AS2 of the first acoustic matching layer 12A, a front end surface BS2 of the second acoustic matching layer 12B, and a front end surface CS2 of the third acoustic matching layer 12C. In addition, FIG. 2 shows an end edge E1 of the first end surface S1 on an acoustic lens 13 side and an end edge E2 of the second end surface S2 on the acoustic lens 13 side. The rear end surface CS1 is a region including the end edge E1. The front end surface CS2 is a region including the end edge E2.

In the example of FIG. 2, the connection portion 11B connects the entire first end surface S1 and the entire second end surface S2 to the support portion 11A. More specifically, the connection portion 11B extends from upper surfaces of both front and rear end parts of the support portion 11A in the upward direction Z1 along the first end surface S1 and the second end surface S2, respectively, and is in contact with the first end surface S1 and the second end surface S2. The connection portion 11B is provided so as to fill a space between the case 15, and the first end surface S1 and the second end surface S2. In the present embodiment, the acoustic lens 13 also covers an upper surface of the connection portion 11B. That is, the connection portion 11B is in contact with the acoustic matching portion 12 and is also in contact with a lower surface of the acoustic lens 13.

The support portion 11A supports the plurality of vibrators 10 and is made of an insulating material that has an absorbent property and that has a vibration damping property to remove unnecessary weak vibrations from a vibration component of the vibrator 10 so as to prevent the ultrasound waves from the vibrator 10 in the downward direction Z2 from returning to an inside of the vibrator 10 again. The support portion 11A has a thermal conductivity higher than a thermal conductivity of the acoustic lens 13. The support portion 11A is mainly made of, for example, a urethane resin, an epoxy resin, a silicone resin, or the like. An electrode 16 connected to each of the ground electrode 10C and the signal electrode 10B is provided in the support portion 11A.

The connection portion 11B is made of an insulating material and is mainly made of, for example, a urethane resin, an epoxy resin, a silicone resin, or the like. The connection portion 11B has a thermal conductivity higher than the thermal conductivity of the acoustic lens 13. With such a relationship of the thermal conductivity, heat generated in the vicinity of a boundary between the acoustic lens 13 and the acoustic matching portion 12 is more easily transferred to a connection portion 11B side having a higher thermal conductivity than the thermal conductivity of the acoustic lens 13. The heat transferred to the connection portion 11B is transferred to the support portion 11A which occupies the majority of the volume in the unit U. Therefore, the safety with respect to the subject under examination can be enhanced by reducing the heat transferred to the acoustic lens 13. In addition, since the connection portion 11B and the acoustic lens 13 are in contact with each other, the above-described heat moved to the acoustic lens 13 can be dissipated to the connection portion 11B and the support portion 11A via a contact surface between the acoustic lens 13 and the connection portion 11B. As a result, the heat transferred to the subject under examination in contact with the acoustic lens 13 can be further reduced.

It is preferable that the connection portion 11B is made of the same material as the support portion 11A. The thermal conductivity of the connection portion 11B may be the same as the thermal conductivity of the support portion 11A, may be lower than the thermal conductivity of the support portion 11A, or may be higher than the thermal conductivity of the support portion 11A. It is preferable that the thermal conductivity of the connection portion 11B is the same as the thermal conductivity of the support portion 11A. In a case where the thermal conductivity of the connection portion 11B and the thermal conductivity of the support portion 11A are made the same, the connection portion 11B and the support portion 11A can be integrally molded using the same material, which makes it possible to reduce the manufacturing cost. In a case where a configuration is employed in which the thermal conductivity of the support portion 11A is higher than the thermal conductivity of the connection portion 11B, the above-described heat can be more efficiently dissipated to a lower side of the ultrasound probe 100, which makes it possible to enhance the heat dissipation performance.

It is preferable that a maximum thickness D1 of the connection portion 11B in the front-rear direction Y is made equal to or greater than an average value of an average thickness of the acoustic lens 13 in the up-down direction Z and a thickness of the third acoustic matching layer 12C, which is in contact with the acoustic lens 13, in the up-down direction Z and is made equal to or less than a size that does not cause an influence on a thickness of the ultrasound probe 100 in the front-rear direction due to a thickness influence of the connection portion 11B. By employing such a configuration, the heat dissipation performance through the connection portion 11B and the support portion 11A can be sufficiently ensured, constraint conditions on the ultrasound probe 100 as a medical device can be satisfied, and the manufacturing can be easily performed.

In the ultrasound probe 100, the connection portion 11B is in contact with the entire first end surface S1 and the entire second end surface S2, but various contact forms between the connection portion 11B and the acoustic matching portion 12 can be employed. For example, the connection portion 11B may be in contact with the front end surface CS2 and the rear end surface CS1 and may not be in contact with the front end surface AS2, the front end surface BS2, the rear end surface AS1, and the rear end surface BS1, in the first end surface S1 and the second end surface S2. Alternatively, the connection portion 11B may be in contact with the front end surface CS2, the front end surface BS2, the rear end surface CS1, and the rear end surface B S1 and may not be in contact with the rear end surface AS1 and the front end surface AS2, in the first end surface S1 and the second end surface S2. Alternatively, the connection portion 11B may be in contact with the front end surface BS2, the front end surface AS2, the rear end surface BS1, and the rear end surface AS1 and may not be in contact with the rear end surface CS1 and the front end surface CS2, in the first end surface S1 and the second end surface S2. Alternatively, the connection portion 11B may be in contact with the front end surface CS2, the front end surface AS2, the rear end surface CS1, and the rear end surface AS1 and may not be in contact with the rear end surface B S1 and the front end surface BS2, in the first end surface S1 and the second end surface S2.

Further, the ultrasound probe 100 has a configuration in which the connection portion 11B is provided between the first end surface S1 and the case 15 and between the second end surface S2 and the case 15, but the heat dissipation performance through the support portion 11A and the connection portion 11B can be ensured even in a case where the connection portion 11B between the first end surface S1 and the case 15 is omitted or the connection portion 11B between the second end surface S2 and the case 15 is omitted.

Figure 3:
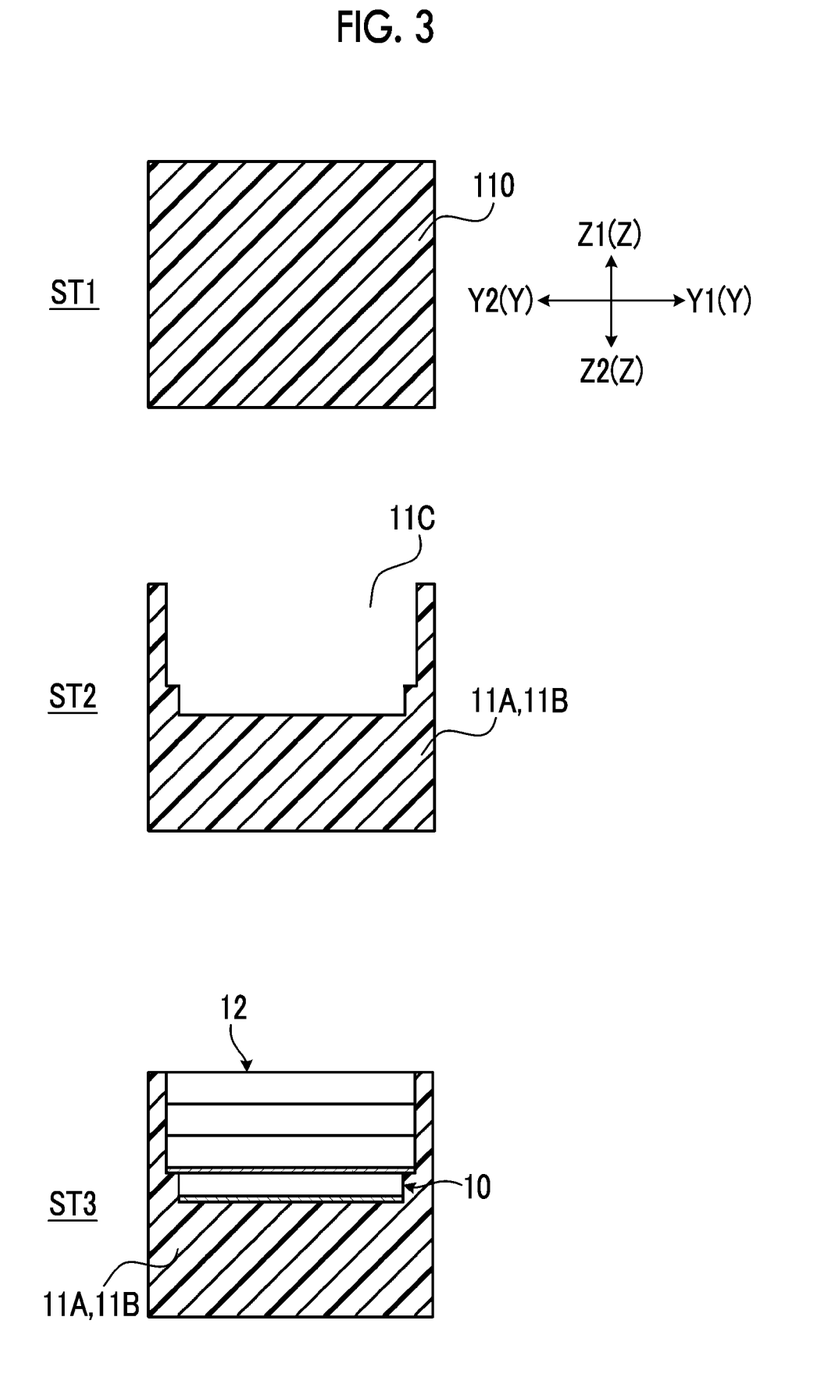
FIG. 3 is a schematic diagram illustrating an example of a manufacturing process of the ultrasound probe 100.

FIG. 3 is a schematic diagram illustrating an example of a manufacturing process of the ultrasound probe 100. First, as shown in a state ST1, a material 110 having a rectangular shape that is long in the left-right direction is prepared. Next, as shown in a state ST2, the material 110 is cut using a machining sensor or the like to form a recessed portion 11C, thereby obtaining an integrally molded product of the support portion 11A and the connection portion 11B. Next, as shown in a state ST3, the vibrator 10 and the acoustic matching portion 12 are sequentially laminated in the recessed portion 11C. After that, the element in the state ST3 is diced to obtain the plurality of units U. After that, a groove obtained through the dicing is filled with an insulating material to form the separation layer 14, and the acoustic lens 13 is formed on the acoustic matching portion 12 and the separation layer 14. The integrally molded product of the support portion 11A and the connection portion 11B as shown in the state ST2 may be formed by using a mold instead of machining. By using the mold, it is possible to reduce the manufacturing cost in a case of performing mass production.

Figure 4:
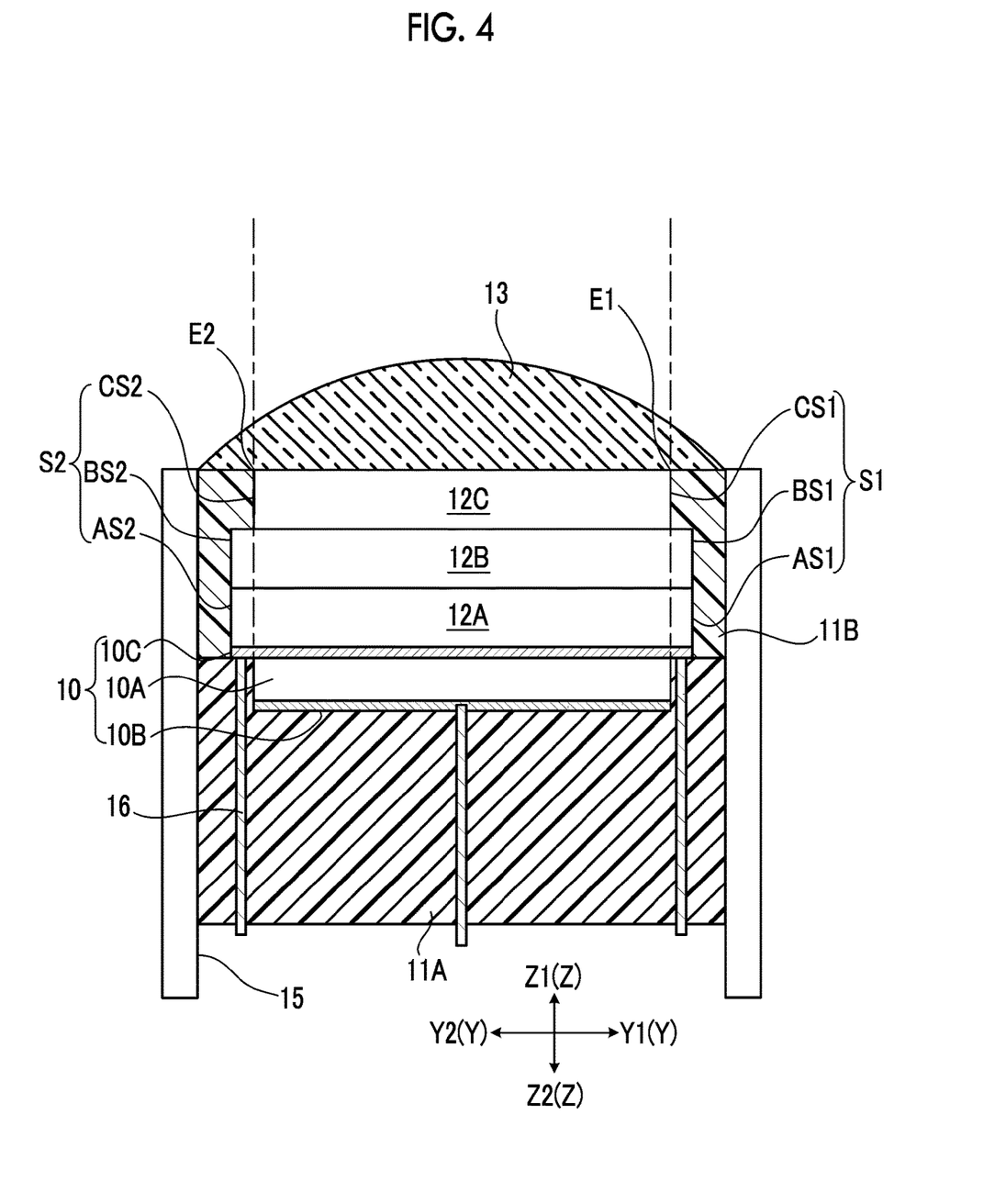
FIG. 4 is a view showing a first modification example of the ultrasound probe 100 and is a schematic cross-sectional view corresponding to FIG. 2.

FIG. 4 is a view showing a first modification example of the ultrasound probe 100 and is a schematic cross-sectional view corresponding to FIG. 2. The ultrasound probe 100 shown in FIG. 4 has the same configuration as that of FIG. 2 except that the width of the third acoustic matching layer 12C in the front-rear direction Y is smaller than the width of each of the second acoustic matching layer 12B and the first acoustic matching layer 12A in the front-rear direction Y. In this modification example, the acoustic matching portion 12 includes the third acoustic matching layer 12C which is a first part of which a width in the front-rear direction Y is a first width, and the second acoustic matching layer 12B and the first acoustic matching layer 12A which are a second part of which a width in the front-rear direction Y is greater than the above-described first width. In addition, the positions of both end edges of the piezoelectric body 10A in the front-rear direction Y and the positions of both end edges of the third acoustic matching layer 12C in the front-rear direction Y coincide with each other. The contact form between the connection portion 11B and the acoustic matching portion 12 is the same as described above.

According to the configuration shown in FIG. 4, the connection portion 11B can also be brought into contact with the upper surface of the second acoustic matching layer 12B. That is, since it is possible to increase a contact area between the acoustic matching portion 12 and the connection portion 11B, it is possible to further enhance the heat dissipation performance through the connection portion 11B and the support portion 11A. In addition, since the maximum thickness of the connection portion 11B also increases, the heat dissipation performance through the connection portion 11B and the support portion 11A can be enhanced.

Figure 5:
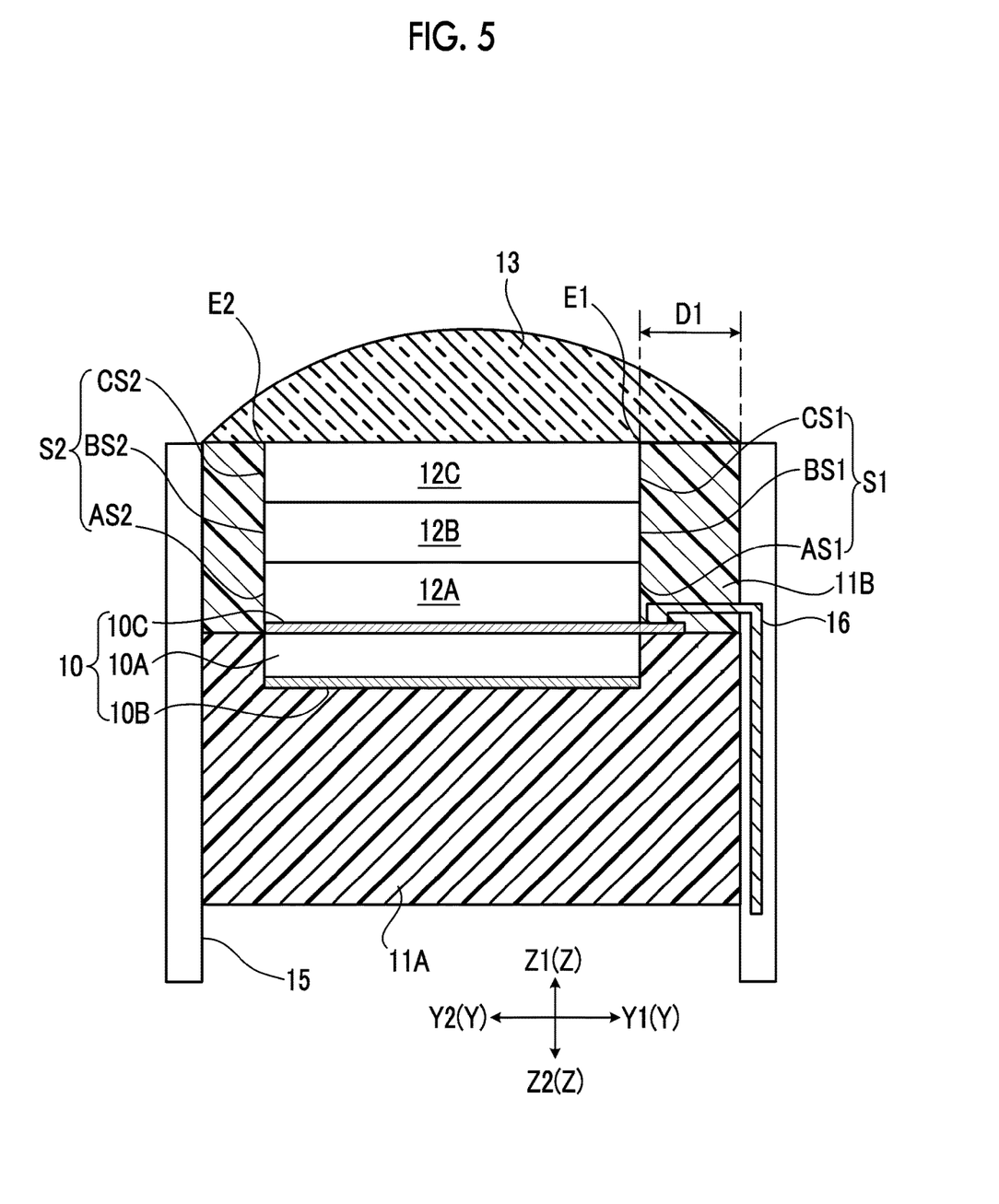
FIG. 5 is a view showing a second modification example of the ultrasound probe 100 and is a schematic cross-sectional view corresponding to FIG. 2.

FIG. 5 is a view showing a second modification example of the ultrasound probe 100 and is a schematic cross-sectional view corresponding to FIG. 2. The ultrasound probe 100 shown in FIG. 5 has the same configuration as that of FIG. 2 except that an end part of the vibrator 10 on one side (rear side) in the front-rear direction Y protrudes toward the one side (rear side) in the front-rear direction Y beyond an end part of the acoustic matching portion 12 on the one side (rear side) in the front-rear direction Y, and that an upper surface of the ground electrode 10C and the electrode 16 are connected in the protruding portion of the vibrator 10.

In the ultrasound probe 100 shown in FIG. 5, a region of the vibrator 10, to which the electrode 16 is connected, contributes little to acoustic radiation. Therefore, the acoustic matching portion 12 need not exist above this region. In the ultrasound probe 100 shown in FIG. 5, since the connection portion 11B exists above this region, the maximum thickness D1 of the connection portion 11B can be made greater than that of the configuration of FIG. 2. By increasing the maximum thickness D1 of the connection portion 11B, it is possible to enhance the heat dissipation performance through the connection portion 11B and the support portion 11A.

Figure 6:
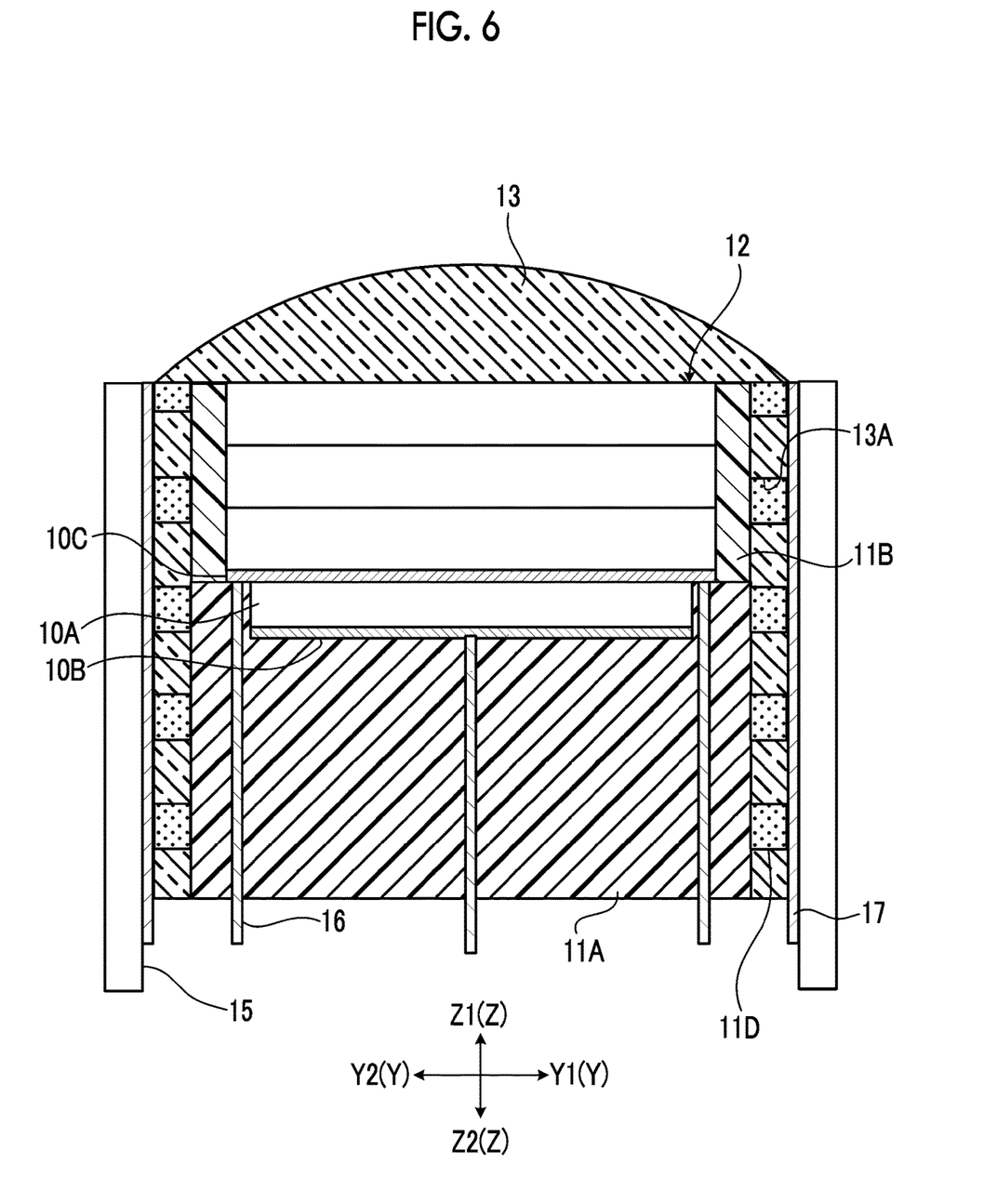
FIG. 6 is a view showing a third modification example of the ultrasound probe 100 and is a schematic cross-sectional view corresponding to FIG. 2.

FIG. 6 is a view showing a third modification example of the ultrasound probe 100 and is a schematic cross-sectional view corresponding to FIG. 2. The ultrasound probe 100 shown in FIG. 6 has the same configuration as that shown in FIG. 2 except that a space between the case 15 and the functional part 11 is filled with a support portion that is integrally formed with the acoustic lens 13 and a part of the acoustic lens 13 holds each unit U, that a plurality of through-holes 13A penetrating in the front-rear direction Y are provided in the support portion which is located between the case 15 and the functional part 11 and a filling layer 11D made of a material having a thermal conductivity higher than the thermal conductivity of the acoustic lens 13 is provided in the through-hole 13A, and that a copper plate 17 is added.

The copper plate 17 has a thickness direction that coincides with the front-rear direction Y and is provided between the case 15 and the support portion composed of a part of the acoustic lens 13. The copper plate 17 constitutes a heat dissipation member that is disposed to face the end surfaces of the support portion 11A and of the connection portion 11B in the front-rear direction Y. The copper plate 17 may be made of a metal other than copper or the like.

The filling layer 11D is made of, for example, the same material as that of the support portion 11A or the connection portion 11B. In the filling layer 11D, one end surface in the front-rear direction Y is in contact with the copper plate 17, and the other end surface in the front-rear direction Y is in contact with the functional part 11.

In the ultrasound probe 100 shown in FIG. 6, since the functional part 11 and the copper plate 17 having a high thermal conductivity are connected to each other through the filling layer 11D, heat generated in the vicinity of the boundary between the acoustic lens 13 and the acoustic matching portion 12 can also be dissipated to the copper plate 17, and the heat dissipation performance can be further enhanced.

The number of the filling layers 11D to be installed (or an installation area) may be changed between a region that overlaps the connection portion 11B when viewed in the front-rear direction Y and a region that overlaps the support portion 11A when viewed in the front-rear direction Y. That is, the contact area between the connection portion 11B and the filling layer 11D and the contact area between the support portion 11A and the filling layer 11D may be different from each other.

For example, in a case where a larger number of the filling layers 11D are provided in the region that overlaps the connection portion 11B when viewed in the front-rear direction Y than in the region that overlaps the support portion 11A when viewed in the front-rear direction Y, it is possible to more efficiently dissipate the heat. A configuration may be employed in which the filling layer 11D is not provided in any one of the region that overlaps the support portion 11A when viewed in the front-rear direction Y or the region that overlaps the connection portion 11B when viewed in the front-rear direction Y.

At least the following matters are described in the present specification.

(1)

An ultrasound probe comprising:
a plurality of vibrators that are arranged in a first direction, each vibrator having a first surface which is located on a side on which the vibrator transmits and receives an ultrasound wave and a second surface opposite to the first surface;
a support portion that supports the second surface of the vibrator;
an acoustic lens that is disposed on a side opposite to a support portion side with respect to the vibrator;
an acoustic matching portion that is disposed between the vibrator and the acoustic lens; and
a connection portion that connects the support portion and at least a partial region of one or both of a first end surface and a second end surface to each other, the first end surface and the second end surface being defined respectively by both end surfaces of the acoustic matching portion in a second direction intersecting the first direction and a direction from the acoustic lens toward the vibrator,
in which the support portion and the connection portion each have a thermal conductivity higher than a thermal conductivity of the acoustic lens.

According to (1), at least a partial region of one or both of the first end surface and the second end surface of the acoustic matching portion and the support portion are connected to each other through the connection portion having a thermal conductivity higher than the thermal conductivity of the acoustic lens, so that heat generated in the vicinity of the boundary between the acoustic matching portion and the acoustic lens can be dissipated from the end surface of the acoustic matching portion to the support portion having a thermal conductivity higher than the thermal conductivity of the acoustic lens. As a result, it is possible to reduce heat transferred to the subject under examination in contact with the acoustic lens, and it is possible to reduce constraints on a driving method of the plurality of vibrators. For example, it is also possible to increase a driving voltage of the vibrator, and it is possible to improve the sensitivity or the image quality of the ultrasound image generated by using the ultrasound probe.

(2)

The ultrasound probe according to (1),
in which the connection portion is in contact with a region including an end edge of one or both of the first end surface and the second end surface, the end edge being located on an acoustic lens side.

According to (2), heat generated in the vicinity of the boundary between the acoustic matching portion and the acoustic lens can be more efficiently dissipated to the support portion.

(3)

The ultrasound probe according to (2),
in which the connection portion is further in contact with the acoustic lens.

According to (3), even in a case where heat generated in the vicinity of the boundary between the acoustic matching portion and the acoustic lens is transferred to the acoustic lens, the acoustic lens and the connection portion are in contact with each other, so that the heat can be dissipated to the support portion via the connection portion. As a result, the heat transferred to the subject under examination in contact with the acoustic lens can be further reduced.

(4)

The ultrasound probe according to any one of (1) to (3),
in which the connection portion and the support portion are made of the same material.

According to (4), the thermal conductivity of the connection portion and the thermal conductivity of the support portion can be made uniform, so that the heat dissipation performance through the connection portion and the support portion can be enhanced. In addition, the manufacturing can be easily performed.

(5)

The ultrasound probe according to any one of (1) to (4),
in which the vibrator includes a piezoelectric body,
in a state viewed in the first direction, the acoustic matching portion includes a first part of which a width in the second direction is a first width and a second part of which a width in the second direction is greater than the first width,
positions of both end edges of the piezoelectric body in the second direction and positions of both end edges of the first part in the second direction coincide with each other, and
the connection portion is in contact with at least the first part.

According to (5), it is possible to increase the contact area between the acoustic matching portion and the connection portion while restraining the influence on the acoustic performance, so that it is possible to further enhance the heat dissipation performance through the connection portion and the support portion.

(6)

The ultrasound probe according to any one of (1) to (4),
in which, in a state viewed in the first direction, an end part of the vibrator on one side in the second direction protrudes toward the one side in the second direction beyond an end part of the acoustic matching portion on the one side in the second direction, and
the connection portion is in contact with at least an end surface of the acoustic matching portion on the one side in the second direction.

According to (6), it is possible to increase the thickness of the connection portion, which is in contact with the acoustic matching portion, in the second direction while restraining the influence on the acoustic performance, so that it is possible to enhance the heat dissipation performance through the connection portion and the support portion.

(7)

The ultrasound probe according to any one of (1) to (6),
in which the acoustic matching portion includes a plurality of layers, and
a maximum thickness of the connection portion in the second direction is equal to or greater than an average value of a thickness of the acoustic lens and a thickness of a layer that is in contact with the acoustic lens among the plurality of layers.

According to (7), sufficient heat dissipation performance through the connection portion and the support portion can be ensured.

(8)

The ultrasound probe according to any one of (1) to (7), further comprising:
- a heat dissipation member that is disposed to face end surfaces of the support portion and of the connection portion in the second direction,
- in which at least one of the support portion or the connection portion is connected to the heat dissipation member.

According to (8), the heat transferred to the connection portion and the support portion can be dissipated to the heat dissipation member, and the heat dissipation performance can be further enhanced.

(9)

An ultrasound diagnostic apparatus comprising:
the ultrasound probe according to any one of (1) to (8).

EXPLANATION OF REFERENCES

S1: first end surface
S2: second end surface
E1, E2: end edge
ST1, ST2, ST3: state
10A: piezoelectric body
10B: signal electrode
10C: ground electrode
10: vibrator
11A: support portion
11B: connection portion
11C: recessed portion
11D: filling layer
11: functional part
12A: first acoustic matching layer
12B: second acoustic matching layer
12C: third acoustic matching layer
12: acoustic matching portion
13: acoustic lens
14: separation layer
15: case
16: electrode
100: ultrasound probe
110: material
AS1, BS1, CS1: rear end surface
AS2, BS2, CS2: front end surface

What is claimed is:

1. An ultrasound probe comprising:
   a plurality of vibrators that are arranged in a first direction, each vibrator having a first surface which is located on a side on which the vibrator transmits and receives an ultrasound wave and a second surface opposite to the first surface;
   a support portion that supports the second surface of the vibrator;
   an acoustic lens that is disposed on a side opposite to a support portion side with respect to the vibrator;
   an acoustic matching portion that is disposed between the vibrator and the acoustic lens; and
   a connection portion that connects the support portion and at least a partial region of one or both of a first end surface and a second end surface to each other, the first end surface and the second end surface being defined respectively by both end surfaces of the acoustic matching portion in a second direction intersecting the first direction and a direction from the acoustic lens toward the vibrator,
   wherein the support portion and the connection portion each have a thermal conductivity higher than a thermal conductivity of the acoustic lens,
   wherein the vibrator includes a piezoelectric body,
   in a state viewed in the first direction, the acoustic matching portion includes a first part of which a width in the second direction is a first width and a second part of which a width in the second direction is greater than the first width,
   positions of both end edges of the piezoelectric body in the second direction and positions of both end edges of the first part in the second direction coincide with each other, and
   the connection portion is in contact with at least the first part.

2. The ultrasound probe according to claim 1,
   wherein the connection portion and the support portion are made of the same material.

3. The ultrasound probe according to claim 1,
   wherein, in a state viewed in the first direction, an end part of the vibrator on one side in the second direction protrudes toward the one side in the second direction beyond an end part of the acoustic matching portion on the one side in the second direction, and
   the connection portion is in contact with at least an end surface of the acoustic matching portion on the one side in the second direction.

4. The ultrasound probe according to claim 1,
   wherein the acoustic matching portion includes a plurality of layers, and
   a maximum thickness of the connection portion in the second direction is equal to or greater than an average value of a thickness of the acoustic lens and a thickness of a layer that is in contact with the acoustic lens among the plurality of layers.

5. The ultrasound probe according to claim 1, further comprising:
   a heat dissipation member that is disposed to face end surfaces of the support portion and of the connection portion in the second direction,
   wherein at least one of the support portion or the connection portion is connected to the heat dissipation member.

6. The ultrasound probe according to claim 1,
   wherein the connection portion is in contact with a region including an end edge of one or both of the first end surface and the second end surface, the end edge being located on an acoustic lens side.

7. The ultrasound probe according to claim 2,
   wherein the connection portion and the support portion are made of the same material.

8. The ultrasound probe according to claim 6,
   wherein, in a state viewed in the first direction, an end part of the vibrator on one side in the second direction protrudes toward the one side in the second direction beyond an end part of the acoustic matching portion on the one side in the second direction, and
   the connection portion is in contact with at least an end surface of the acoustic matching portion on the one side in the second direction.

9. The ultrasound probe according to claim 6,
   wherein the acoustic matching portion includes a plurality of layers, and
   a maximum thickness of the connection portion in the second direction is equal to or greater than an average value of a thickness of the acoustic lens and a thickness of a layer that is in contact with the acoustic lens among the plurality of layers.

10. The ultrasound probe according to claim 6, further comprising:
a heat dissipation member that is disposed to face end surfaces of the support portion and of the connection portion in the second direction,
wherein at least one of the support portion or the connection portion is connected to the heat dissipation member.

11. The ultrasound probe according to claim 2,
wherein the connection portion is further in contact with the acoustic lens.

12. The ultrasound probe according to claim 11,
wherein the connection portion and the support portion are made of the same material.

13. The ultrasound probe according to claim 11,
wherein, in a state viewed in the first direction, an end part of the vibrator on one side in the second direction protrudes toward the one side in the second direction beyond an end part of the acoustic matching portion on the one side in the second direction, and
the connection portion is in contact with at least an end surface of the acoustic matching portion on the one side in the second direction.

14. The ultrasound probe according to claim 11,
wherein the acoustic matching portion includes a plurality of layers, and
a maximum thickness of the connection portion in the second direction is equal to or greater than an average value of a thickness of the acoustic lens and a thickness of a layer that is in contact with the acoustic lens among the plurality of layers.

15. The ultrasound probe according to claim 11, further comprising:
a heat dissipation member that is disposed to face end surfaces of the support portion and of the connection portion in the second direction,
wherein at least one of the support portion or the connection portion is connected to the heat dissipation member.

16. An ultrasound diagnostic apparatus comprising:
the ultrasound probe according to claim 1.

* * * * *